United States Patent [19]

Benincasa

[11] Patent Number: 5,891,891
[45] Date of Patent: Apr. 6, 1999

[54] USE OF IMIDAZO [1, 2-A] PYRIDINE-3-ACETAMIDE DERIVATIVES FOR THE THERAPEUTIC TREATMENT OF NEUROPSYCHIATRIC SYNDROMES ASSOCIATED WITH DISFUNCTION OF THE NEURAL CIRCUITS OF THE BASAL GANGLIA

[75] Inventor: Elena Benincasa, Rome, Italy

[73] Assignee: Clarendon-Trading & Investimentos LDA, Madeira, Portugal

[21] Appl. No.: 930,644

[22] PCT Filed: Apr. 2, 1996

[86] PCT No.: PCT/IT96/00063

§ 371 Date: Nov. 18, 1997

§ 102(e) Date: Nov. 18, 1997

[87] PCT Pub. No.: WO96/31210

PCT Pub. Date: Oct. 10, 1996

[30] Foreign Application Priority Data

Apr. 7, 1996 [IT] Italy .................. RM95A0223

[51] Int. Cl.⁶ .................. A61K 31/44; A61K 31/415
[52] U.S. Cl. .................................................. 514/300
[58] Field of Search ................................. 514/300

[56] References Cited

U.S. PATENT DOCUMENTS

| | | | |
|---|---|---|---|
| 5,032,595 | 7/1991 | Krueger et al. ................ | 514/300 |
| 5,206,382 | 4/1993 | Costa et al. .................... | 548/494 |

FOREIGN PATENT DOCUMENTS 0 050 563  4/1982  European Pat. Off. .

OTHER PUBLICATIONS

Annals of Neurology, vol. 39, No. 3, Mar. 1996, pp. 368–377, XP002008555, K.G. Rottach et al, "Dynamic Properties of Horizontal and Vertical Eye Movements in Parkinsonian Syndromes".
ACTA Psychiatr. Scand., vol. 80, No. 2, Aug. 1989, pp. 137–141, XP002008556, M. Casacchia et al, "A double–blind, placebo–controlled study of alpidem, a novel anxiolytic of imidazopyridine structure. . . ".
Database Embase, Elsevier Science Publishers, Amsterdam, NL, Accession No. 92058496, 1992, Abou–Gharbia et al, XP002008559, "IV Congress of the ECNP"; Drug News Perspect., vol. 4, No. 10, 1991, pp. 647–650.
Am. Pharm., vol. 34, No. 3, Mar. 1994, pp. 24–59, XP002008557, D.A. Hussar, "New Drugs of 1993".
Sem. Hop., vol. 67, No. 42–43, 1991, pp. 1905–1908, XP002008558, D. Ginestet et al, "Anxiete et insomnie: Quelles alternatives medicamenteuses aux benzodiazepines?".

Primary Examiner—Phyllis G. Spivack
Attorney, Agent, or Firm—Griffin, Butler Whisenhunt & Szipl, LLP

[57] ABSTRACT

Treatment of Parkinson's disease, parkinsonian syndromes, extrapyramidal syndromes, obsessive-compulsive disorder and syndromes, and frontal and subcortical dementias, with imidazo[1,2-a]pyridine-3-acetamide derivatives of the formula (I)

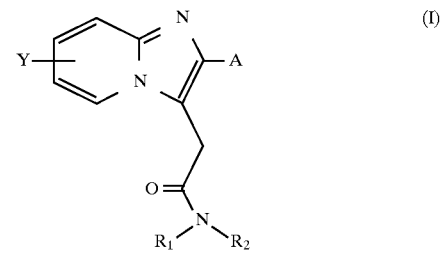

wherein Y represents a hydrogen or halogen atom or a $C_{1-4}$ alkyl group, A represents naphthyl or $C_6H_3X_1X_2$, wherein each of $X_1$ and $X_2$ independently of one another is a hydrogen or halogen atom, a $C_{1-4}$ alkoxy group, a $C_{1-6}$ alkyl group or $CF_3$, $CH_3S$—, $CH_3SO_2$— or —$NO_2$, and each of $R_1$ and $R_2$ independently of one another represents either a hydrogen atom, or a straight or branched $C_{1-5}$ alkyl group which is unsubstituted or substituted by one or more halogen atoms, hydroxyl, —$N(C_{1-4}$ alkyl$)_2$, carbamoyl or $C_{1-4}$ alkoxy groups, or an allyl group, or a propargyl group, or a $C_{3-6}$ cycloalkyl group, or a benzyl group, or a phenyl group, not both $R_1$ and $R_2$ being hydrogen, or —$NR_1R_2$ represents a heterocyclic ring containing from 3 to 6 carbon atoms, or a heterocyclic ring of the formula

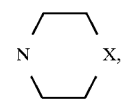

wherein X is O, S, CHOR' or N—R, R' being hydrogen or benzyl and R being hydrogen, a $C_{1-4}$ alkyl group, or phenyl which is unsubstituted or substituted by methoxy or a halogen atom, provided that if Y is 6-chloro, A is not 4-chlorophenyl.

3 Claims, No Drawings

USE OF IMIDAZO [1, 2-A] PYRIDINE-3-ACETAMIDE DERIVATIVES FOR THE THERAPEUTIC TREATMENT OF NEUROPSYCHIATRIC SYNDROMES ASSOCIATED WITH DISFUNCTION OF THE NEURAL CIRCUITS OF THE BASAL GANGLIA

The present invention relates to a new therapeutic use of imidazo[1,2-a]pyridine-3-acetamide derivatives in the treatment of Parkinson's disease, parkinsonian syndromes, other extrapyramidal syndromes ("parkinsonism plus"), obsessive-compulsive disorder and other obsessive-compulsive syndromes, and frontal and subcortical dementias.

Such imidazo[1,2-a]pyridine-3-acetamide derivatives are disclosed in EP-B-0 050 563 and have the general formula (I)

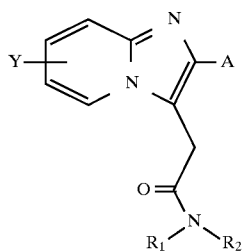

wherein

Y represents a hydrogen or halogen atom or a $C_{1-4}$ alkyl group,

A represents a naphthyl radical or a radical

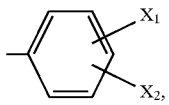

wherein each of $X_1$ and $X_2$ independently of one another is a hydrogen or halogen atom, a $C_{1-4}$ alkoxy group, a $C_{1-6}$ alkyl group or $CF_3$, $CH_3S$—, $CH_3SO_2$— or —$NO_2$, and each of $R_1$ and $R_2$ independently of one another represents either a hydrogen atom, or a straight or branched $C_{1-5}$ alkyl group which is unsubstituted or substituted by one or more halogen atoms, hydroxyl, —$N(C_{1-4}$ alkyl$)_2$, carbamoyl or $C_{1-4}$ alkoxy groups, or an allyl group, or a propargyl group, or a $C_{3-6}$ cycloalkyl group, or a benzyl group, or a phenyl group, not both $R_1$ and R2 being hydrogen, or —$NR_1R_2$ represents a heterocyclic ring containing from 3 to 6 carbon atoms, or a heterocyclic ring of the formula

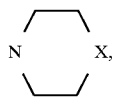

wherein X is O, S, CHOR' or N—R, R' being hydrogen or benzyl and R being hydrogen, a $C_{1-4}$ alkyl group, or phenyl which is unsubstituted or substituted by methoxy or a halogen atom, provided that, if Y is 6-chloro, A is not 4-chlorophenyl.

Among these imidazo[1,2-a]pyridine-3-acetamide derivatives, imidazo[1,2-a]pyridine-3-acetamides of the following formula (II)

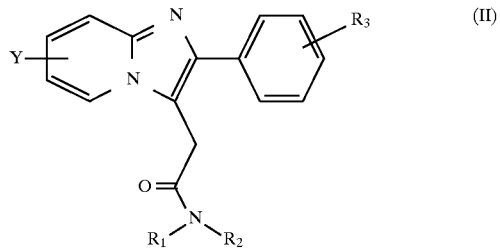

wherein $R_3$ is halogen, preferably chlorine, or a $C_{1-4}$ alkyl group;

Y is halogen, preferably chlorine, or a $C_{1-4}$ alkyl group; and $R_1$ and $R_2$, equal or different, are hydrogen or a $C_{1-4}$ alkyl group, provided that, if Y is 6-chloro, $R_3$ is not 4-chloro, are particularly preferred and zolpidem [N,N,6-trimethyl-2-(4-methylphenyl)imidazo[1,2-a]pyridine-3-acetamide hemitartrate] is especially preferred.

The invention also relates to a pharmaceutical composition comprising the above mentioned active principle and at least one pharmacologically acceptable excipient. The composition, in unit dosage form, preferably comprises from 5 to 20 mg of active principle.

Zolpidem [N,N,6-trimethyl-2-(4-methylphenyl)iznidazo[1,2-a]pyridine-3acetamide hemitartrate] has until now been used exclusively as a hypnotic drug. For the treatment of insomnia, 5–20 mg of zolpidem are taken on retiring.

Zolpidem is absorbed rapidly and completely, even when orally administered. The absolute bioavailability in man is approximately 70%. When 10 mg of zolpidem are orally administered to healthy volunteers, the peak plasma level is reached after 0.5–3 hours and the plasma half-life is 0.7–3.5 hours. The fraction that remains unbound to the plasma proteins is approximately 8% (Thenot et al., Pharmacokinetics and metabolism of zolpidem in various animal species and in humans, in: Sauvanet, Langer and Morselli, Imidazopyridines in sleep disorders, Raven Press, NY, 1988; Depoortere et al., Zolpidem, a novel non-benzodiazepine hypnotic, I. Neuropharmacological and behavioural effects, J. Pharmacol. Exp. Ther., 237:649–60, 1986).

Although zolpidem has effects characteristic of benzodiazepines, these appear in a different order as the dose is increased. The sedative and hypnotic effects are produced by much lower doses than are required to produce its other effects (anticonvulsant, anxiolytic and muscle-relaxant) (Zivkovic et al., P. Barthouil (Ed.), Insomnie et Imidazopyridines, Excerpta Medica, 1990). Zolpidem reduces the sleep onset latency and the number of nocturnal awakenings, thereby increasing the total sleep time. Flumazenil antagonizes all the effects of zolpidem, as it does those of the benzodiazepines (Depoortere et al., Zolpidem, a novel non-benzodiazepine hypnotic, I. Neuropharmacological and behavioural effects, J. Pharmacol. Exp. Ther., 237:649–60, 1986). The acute, subacute and chronic toxicity of zolpidem are minimal (J. C. Friedmann, A. Prenez, Safety evaluation of zolpidem, in: Sauvanet, Langer, Morselli, Imidazopyridines in sleep disorders, Raven Press, NY, 1988).

Study of safety profile in patients indicate that zolpidem is a safe drug, which may induce adverse events that are usually dose-related and may be considered as extentions of its pharamacological properties. Such adverse events include vertigo, headache and confusion (R. Palminteri, G. Narbonne, Safety profile of zolpidem, in: Sauvanet, Langer, Morselli, Imidazopyridines in sleep disorders, Raven Press, NY, 1988).

Zolpidem differs from benzodiazepines in that it has an atypical profile of binding with the ω receptor sites. The GABA-A receptor complex comprises the receptor for GABA-A, the channel for the Cl— ion and the ω site (recognition site for benzodiazepines, imidazopyridines, cyclopyrrolones). Zolpidem interacts with the ω sites and, like the benzodiazepines, potentiates the response of the receptor to GABA by increasing the frequency with which the Cl— channels are opened in response to GABA. The majority of benzodiazepines have a poor selectivity for the various subtypes of ω receptor ($\omega_1$, $\omega_2$ and $\omega_3$).

By contrast, it is important to point out that many imidazo[1,2-a]pyridine-3acetamides (including zolpidem) show a high selectivity for the $\omega_1$ ($BZ_1$) receptor subtype (Langer et al., zolpidem and alpidem: two imidazopyridines with selectivity for $\omega_1$- and $\omega_3$-receptor subtypes, in: G. Biggio, E. Costa (Eds.), GABA and benzodiazepine receptor suptypes, Raven Press, NY, 1990).

In vitro studies and in vivo studies in rats and monkeys show that zolpidem binds selectively to subtype $BZ_1$ ($\omega_1$) of the benzodiazepine receptors. Studies conducted in vitro (Arbilla et al., Pharmacological profile of the imidazopyridine zolpidem at benzodiazepine receptors and electrocorticogram in rats, Naunyn-Schmiedeberg's Arch. Pharmacol., 330:248–251, 1985) and in vivo (Zivkovic et al., P. Bathouil (Ed), Insomnie et Imidazopyridines, Excerpta Medica, 1990) show that zolpidem is more effective than the benzodiazepines in inducing effects mediated by GABAergic mechanisms.

The highest density of $BZ_1$ receptors is found in the ventral globus pallidus and the substantia nigra pars reticulata (Langer et al., Receptors involved in the mechanism of action of zolpidem, in: Sauvanet, Langer and Morselli, Imidazopyridines in sleep disorders, Raven Press, 1988), the two output structures of the basal ganglia. In other structures of the central nervous system (CNS), by contrast, $BZ_2$ receptors either predominate (caudate nucleus, putamen) or both $BZ_1$ and $BZ_2$ receptor are present (frontoparietal cortex, thalamus).

However, there is no correlation between the already known therapeutic use of zolpidem as a hypnotic and that which constitutes the subject of the present invention.

It has now been found that zolpidem is effective in the therapeutic treatment of Parkinson's disease, parkinsonian syndromes, other extrapyramidal syndromes ("parkinsonism plus"), obsessive-compulsive disorder and other obsessive-compulsive syndromes, and frontal and subcortical dementias.

Parkinson's disease (PD) is characterized by the appearance of degenerative lesions in the substantia nigra pars compacta and its dopaminergic projections into the striatum (caudate nucleus and putamen). Clinically, the disease is characterized by the presence of at least two of the following three cardinal signs: bradykinesia, rigidity, tremor. In Caucasian populations, the prevalence of PD ranges from 84 to 187 cases per 100,000 people.

In PD, the reduced dopaminergic innervation of the striatum gives rise, via two separate circuits (direct and indirect), to excessive activity of the internal segment of globus pallidus (Vitek et al., Soc. Neurosci. Abstracts, 19:1584, 1993), which has inhibitory effects on the following two structures:

(a) on the ventrolateral nucleus of the thalamus, resulting in reduced excitation by the thalamus of some areas of the cerebral cortex, in particular the supplementary motor area (L. Coté, M. D. Crutcher, The basal ganglia, in: E. R. Kandel, J. H. Schwartz, T. M. Jessel (Eds.), Principles of Neural Sciences, Elsevier, 1991);

(b) on the pedunculopontine nucleus, resulting in reduced excitation of the vestibulospinal and reticulospinal descending pathways.

This inhibitory hyperactivity of the internal segment of globus pallidus seen in PD is achieved via the following two circuits: (1) "direct" circuit: in this circuit dopamine has excitatory effects, mediated by D1 receptors. Hence in PD the reduced dopaminergic nigrostriatal excitation of the putaminal neurons that project into the internal segment of globus pallidus reduces the inhibition by the putamen of the internal globus pallidus, which is therefore excited; (2) "indirect" circuit: in this circuit the dopamine has inhibitory effects, mediated by D2 receptors. Hence in PD the reduced dopaminergic nigrostriatal inhibition of the putaminal neurons that project into the external segment of globus pallidus causes increased putaminal inhibition of the external globus pallidus, thereby reducing the inhibitory effect of the external globus pallidus on the subthalamic nucleus; as a result the subthalamic nucleus is excited and in turn excites the internal segment of globus pallidus.

For many years, the drug most widely used in the treatment of PD has been levodopa (L-dopa), the metabolic precursor of dopamine, which is not capable of crossing the blood-brain barrier. Most of L-dopa is metabolized peripherally before it reaches its sites of action in the CNS. Hence L-dopa used alone has antiparkinsonian effects only in very high doses that frequently cause severe side effects (loss of appetite, nausea and vomiting, orthostatic hypotension, etc.)

It is therefore expedient to combine L-dopa with drugs that produce peripheral inhibition of the enzyme dopa-decarboxylase. These drugs (benserazide and carbidopa) prevent L-dopa being metabolized peripherally (that is before it reaches the CNS) and therefore reduce the doses of L-dopa needed to achieve the therapeutic effects, thereby also reducing the abovementioned side effects.

In patients with PD, prolonged treatment with L-dopa (even if administered in combination with peripheral dopa-decarboxylase inhibitors) can often produce other unpleasant side effects, such as the commonly seen dyskinesias (choreiform movements of the head, trunk and limbs) caused by hypersensitivity to L-dopa.

The major disadvantage of treatment with L-dopa is that, with time, this drug can lose its initial efficacy in patients with PD. After a few years' continuous treatment with L-dopa, the parkinsonian symptoms tend to become increasingly less controlled by this drug. The onset of fluctuations in motor performance (on-off fluctuations) is also common: "on" periods, characterized by good motor performance lasting for a few hours after a dose of L-dopa has been taken, alternating throughout the day with "off" periods, characterized by exacerbation of the motor symptoms. These on-off effects are not observed prior to the start of treatment with L-dopa.

The progressive loss of efficacy of L-dopa in patients with PD poses a number of complex therapeutic problems. It has been suggested that it is helpful to start by administering this drug in the lowest dose possible. However, there is now discussion as to the advisability of using L-dopa at all in the early stages of the disease.

Dopamine-agonist drugs (bromocriptine, lisuride, pergolide) act directly on the dopaminergic receptors and offer a possible alternative to L-dopa, in combination with which they can also be used. However, dopamine-agonist drugs can also give rise to major side effects (psychiatric disturbances, nausea, vomiting, hypotension, erythromelalgia). These effects, like those of L-dopa, can be severe enough to necessitate the treatment being suspended.

Research into the drug treatment of PD is currently examining the following classes of drugs: new dopaminergic agonists, catechol-O-methyl-transferase inhibitors, antagonists of the glutamergic NMDA receptors, glutamate release inhibitors (D. B. Calne, Treatment of Parkinson's Disease, N. Engl. J. Med., 329:1021–1027, 1993).

It has been previously suggested that, in theory, drugs that act on the GABAergic system may be of value in PD (J. Jankovich, C. D. Marsden, Therapeutic strategies in Parkinson's disease, in: J. Jankovich, E. Tolosa (Eds.), Parkinson's disease and movement disorders, Urban & Schwarzenberg, 1988). However, there is very little experimental evidence indicating that these drugs might prove effective in reality. There have been isolated reports of a slight beneficial effect in PD patients following the administration of progabide, a GABA-agonist that is thought to reduce the "wearing off" effect (K. J. Bergman, Progabide: a new GABA-mimetic agent clinical use, Clin. Neuropharmacol., 8:6–13, 1985).

Recently, there have also been reports that a new neurosurgical approach consisting in the induction of stereotaxic lesions of the posteroventral globus pallidus is effective in patients with PD (Laitinen et al., Leksell's posteroventral pallidotomy in the treatment of Parkinson's disease, J. Neurosurg., 76:53–61, 1992; Iacono and Lonser, Reversal of Parkinson's akinesia by pallidotomy, Lancet 343:418–419, 1994). This approach is apparently more effective than transplants of foetal tissue and is capable of improving all three cardinal symptoms of the disease (akinesia, rigidity, tremor).

The therapeutic effect of this procedure is due to the interruption of the projections that originate from the internal segment of globus pallidus and are directed to (a) the thalamus (ventrolateral nucleus) on the one hand and (b) the pedunculopontine nucleus on the other (J. E. Hoover, P. L. Strick, Multiple output channels in the basal ganglia, Science 259:819–821, 1993).

The inventor's first observation of the efficacy of zolpidem in the treatment of Parkinson's disease was made in a 62-year-old female patient who had been prescribed zolpidem as a sleep-inducing agent. This patient had been suffering from Parkinson's disease for many years and had also developed, about two years previously, obsessive-compulsive behaviour and dementia as a result of subcortical ischaemic cerebrovascular lesion in the putamen of the left hemisphere. The mental deterioration exhibited by the patient could be defined as subcortical dementia, with characteristics similar to those of frontal dementias (M. A. Albert et al., The "subcortical dementia" of progressive supranuclear palsy, J. Neurol. Neurosur. Psychiat. 37:121–130, 1974; R. D'Antona et al., Subcortical dementia. Frontal cortex hypometabolism detected by positron tomography in patients with progressive supranuclear palsy, Brain 108:785–799, 1985). The obsessive-compulsive behaviour was characterized principally by constant verbal iterations (compulsive repetition of words or phrases throughout most of the day).

It should be stressed that obsessive-compulsive disorder, like Parkinson's disease, also seems to be due to a dysfunction of neural circuits involving the basal ganglia (J. L. Cummings, K. Cunningham, Obsessive-compulsive disorder in Huntington's disease, Biol. Psychiatry 31:263–270, 1992; Laplane et al.,Obsessive-compulsive and other behavioural changes with bilateral basal ganglia lesions, Brain 112:699–725, 1989).

After taking 10 mg of zolpidem the patient showed no signs of drowsiness, but she did show a marked improvement in both the parkinsonian symptoms (akinesia and rigidity) and the obsessive-compulsive symptoms (cessation of the verbal iterations). The patient also appeared to show some cognitive improvement, with surprising remission of the symptoms of dementia.

A placebo-controlled double-blind study was conducted in this patient to evaluate the possible effects of various substances on the parkinsonian and compulsive symptoms.

Zolpidem was administred on two separate occasions and produced antiparkinsonian effects equivalent to those of L-dopa. Drugs that are agonists of the BZ sites but have no selectivity for the $BZ_1$ receptor, such as triazolam (benzodiazepine with a short half-life) and zopiclone (cyclopyrrolone), had no effect on the parkinsonian symptoms.

Zolpidem, administered on 2 separate occasions, also both eliminated the obsessive and compulsive symptoms and produced a marked improvement in cognitive performance in neuropsychological tests, with almost complete remission of the dementia.

By contrast, neither L-dopa nor zopiclone had any effect on the compulsive behaviour or cognitive performance. Triazolam had only a slight effect on the compulsive behaviour and cognitive performance.

As a result of this first observation, a placebo-controlled double-blind study was conducted in ten patients who had been clinically diagnosed as suffering from PD using the criteria of Ward and Gibb (C. D. Ward, W. R. G. Gibb, Research diagnostic criteria for Parkinson's disease. Adv. Neurol., 53:245–249, 1990).

The demographic and clinical characteristics of the group of the patients with PD are shown in Table 1.

TABLE 1

| Characteristics of the PD group | |
| --- | --- |
| Total number | n = 10 |
| Sex ratio (m/f) | 3/7 |
| Mean age (SD) | 69.9 (12.0) yrs |
| Mean disease duration (SD) | 9.0 (6.8) yrs |
| Mean Hoehn-Yahr score (SD) | 2.9 (1.2) |

The severity of the motor signs was assessed using the motor examination part of the Unified Parkinson's Disease Rating Scale (UPDRS-III) (S. Fahn, R. L. Elton, United Parkinson's Disease Rating Scale Developmental Commitee, United Parkinson's Disease Rating Scale, in: S. Fahn et al., Recent developments in Parkinson's disease, MacMillan, 1987). In accordance with the current criteria in the literature, a motor improvement equal to a cutoff value of 20% reduction in the score on UPDRS-III was considered significant (T. Gasser et al., Apomorphine test for dopaminergic responsiveness in patients with previously untreated Parkinson's disease, Arch. Neurol. 49:1131–1134, 1992.

Zolpidem was administered in a single oral dose of 10 mg. The effect was evaluated one hour after administration. The results are shown in Table 2.

We found that zolpidem, unlike placebo, produced a significant improvement in the motor symptons in the group of patients with PD taken as a whole.

TABLE 2

| Scores obtained on UPDRS-III by the group of patients with PD | | |
| --- | --- | --- |
| UPDRS-III scores: | Mean (SD) | |
| placebo | | |
| baseline | 41.1 (21.9) | |
| 1 hr after administr. | 40.4 (21.4) | p = n.s. |
| % improvement | 0.8 (7.1) | |
| zolpidem | | |
| baseline | 43.5 (22.1) | |

TABLE 2-continued

Scores obtained on UPDRS-III by the group of patients with PD

| UPDRS-III scores: | Mean (SD) | |
|---|---|---|
| 1 hr after administr. | 33.9 (18.2) | p < 0.009 |
| % improvement | 19.4 (20.7) | |

Statistical method: Wilcoxon Signed Rank Test

In particular, our results show that in 6 out of 10 patients zolpidem produced a significant improvement of ≧20% in the parkinsonian symptoms. The percentage improvement ranged in the responders between 21% and 65%.

In the patients who responded favourably to zolpidem there were improvements in rigidity, akinesia and bradykinesia, resulting in positive effects on posture and gait. There were also improvements in facial expression and resting and postural tremor.

At this point we analysed separately the performances of two subgroups of patients with PD, i.e. responders and non-responders to zolpidem (Table 3).

TABLE 3

UPDRS-III Scores in Responder and Non-responder PD Patients

| | Responders | Non-responders |
|---|---|---|
| placebo | | |
| baseline | 44.0 (22.8) | 36.7 (23.1) |
| 1 hr after | 43.2 (23.7) | 36.2 (20.0) |
| % improv. | 2.3 (7.5) | −1.5 (6.9) |
| zolpidem | | |
| baseline | 46.2 (24.0) | 39.5 (21.7) |
| 1 hr after | 30.3 (16.8) | 39.2 (21.4) |
| % improv. | 31.9 (16.7) | 0.6 (5.9) |

Statistical method: Kolmogorov-Smirnov

The results of this analysis show that the mean percentage motor improvement was 31.9% in the responders subgroup and 0.6% in the non-responders.

The two subgroups of patients did not differ significantly in terms of age, duration of disease or severity of PD (Table 4).

TABLE 4

Characteristics of Responder and Non-responder PD Patients

| | Responders (n = 6) | non-responders (n = 4) | |
|---|---|---|---|
| Age | 68.0 (13.9) | 72.7 (9.6) | p = n.s. |
| Duration | 10.0 (8.4) | 7.5 (4.2) | p = n.s. |
| Hoehn-Yahr | 3.0 (1.1) | 2.7 (1.5) | p = n.s. |

Statistical method: Kolmogorov-Smirnov

Despite this, the mean duration of disease appeared to be longer and the severity greater in the responders, though the differences were not significant. The difference in the duration of disease between the two groups was 25% on average. The difference in the severity was 10% if calculated using the Hoehn-Yahr scale, but 14.5–16.6% if calculated on the basis of the scores obtained on UPDRS-III in baseline conditions (i.e. without treatment).

The limited number of patients with PD in our sample probably does not allow definitive conclusions to be drawn about the possibility of identifying different clinical or demographic characteristics in the two subgroups of patients with PD (responders and non-responders to zolpidem).

However, it is interesting to note that there was a significant improvement in the motor symptoms of PD in 3 of 4 most severely affected patients (patients Nos. 1, 2, 10) and in 3 of the 6 less severely affected patients (patients Nos. 3, 4, 7). Of the 4 patients who showed no significant improvements, three had mild PD (patients Nos. 5, 6, 8) and one had severe PD (patient No. 9).

Two severely affected patients (Nos. 1 and 2) were also given L-dopa under double-blind conditions. The antiparkinsonian effects of zolpidem were substantially comparable to those of L-dopa in both cases (improvements observed in patient No. 1: zolpidem=+29.5%, L-dopa=+26.6%; improvements observed in patient No. 2: zolpidem=+65.2%, L-dopa=+69%). Patients Nos. 1, 2 and 7 were also treated with zolpidem on a long-term basis (for up to 4 years); this produced satisfactory results with improvement in UPDRS scores ranging from 27% to 52%. These patients received the drug orally in a dosage of up to 50–60 mg/day, divided into 3 or 4 daily doses. Thus, the drug had an effective antiparkinsonian action under these conditions, with no significant side effects (in particular no drowsiness).

It is interesting to note that zolpidem produced no drowsiness in six out of ten patients. In particular, no drowsiness was observed in three of the four most severely affected patients. The drowsiness observed in four patients varied in intensity: one patient (No. 3) exhibited only mild drowsiness whereas two others (Nos. 4 and 6) showed moderate drowsiness, though this did not prevent them from cooperating during the motor test on the UPDRS. Finally, patient No. 9, who had severe PD, exhibited extreme drowsiness which made it difficult for her to cooperate during the motor test on the UPDRS.

The results of this clinical study show that, at least in a subpopulation of patients with PD, zolpidem is effective as an antiparkinsonian drug.

With regard to the lack of response to zolpidem observed in patients Nos. 5, 6, 8 and 9, it should be stressed that even L-dopa, when administered acutely in a population of patients with PD of varying severity, fails to produce significant improvements in the motor symptoms in some 20% of patients. This percentage of non-responders to acute administration is even higher in patients with mild PD ( A. J. Hughes, A. J. Lees, G. M. Stern, Apomorphine test to predict dopaminergic responsiveness in Parkinsonian syndromes, Lancet 336(2):32–34, 1990).

It can therefore be postulated that imidazopyridines will be particularly effective in a subpopulation of parkinsonian patients possibly with a more severe form of the disease. The only side effect observed was drowsiness, though this was inconstant and varied in intensity. It is also surprising that zolpidem, a hypnotic drug, should have little, if any, sleep-inducing effect, at least in a subpopulation of patients with PD.

In the rat, following the induction of experimental striatal lesions with cainate, increased binding of benzodiazepines was observed in the globus pallidus, the substantia nigra pars reticulata and the entopeduncolar nucleus (Pan et al., Characterization of benzodiazepine receptor changes in substantia nigra, globus pallidus and entopeduncular nucleus after striatal lesions, J. Pharmacol. Exper. Therapeutics, 230:768–775, 1984). It can be postulated that in PD, too, there may be an up-regulation of the BZ receptors in the globus pallidus and/or the substantia nigra pars reticulata, with a consequently increased response to GABA-BDZ receptor agonists. These structures are crucial to the pathophysiology of PD, not having a clear role in sleep induction. An up-regulation phenomenon in the internal segment of globus pallidus and/or substantia nigra pars reticulata could on the one hand explain the therapeutic effects of zolpidem in PD and on the other account for the fact that in patients with PD zolpidem may have no sleep-inducing effect, or at least a lesser hypnotic effect than that commonly observed in normal subjects.

Theoretically, an interesting analogy can also be drawn between the pharmacological effect of zolpidem in inducing selective inhibition of the internal segment of globus pallidus and the effects of neurosurgery in the form of posteroventral pallidotomy. Both forms of treatment can have therapeutic effects on all the cardinal symptoms of PD. Clearly, the availability of an effective alternative form of drug treatment, based on administration of zolpidem, for patients with PD who have ceased to respond to L-dopa could in some cases represent a valid solution which would enable the risks and complications of neurosurgery to be avoided.

We also conducted a placebo-controlled double-blind study in a 59-year-old patient with Steele-Richardson-Olszewski syndrome (progressive supranuclear palsy). This male patient had been suffering from this disease for 4 years. The oral administration of zolpidem (10 mg) produced an improvement in numerous clinical signs such as dysarthria, supranuclear vertical and lateral gaze palsy, akinesia and bradykinesia, postural stability and gait.

The patient's score on UPDRS-III (which takes account of many of the motor symptoms of Steele-Richardson-Olszewski syndrome) fell from 39 (baseline, without drug) to 26 (after zolpidem), indicating a significant motor improvement (+33%), while the improvement in the UPDRS-III score after placebo was not significant (+5%).

The significance of this observation lies in the fact that patients with Steele-Richardson-Olszewski syndrome rarely respond to drug treatment (A. J. Hughes, A. J. Lees, G. M. Stern, Apomorphine test to predict dopaminergic responsiveness in Parkinsonian syndromes, Lancet, 336 (2):32–34, 1990).

In a recent post-mortem study of cerebral tissue from patients with Steele-Richardson-Olszewski syndrome there was shown to be a reduction in GABAergic transmission in the striatum and globus pallidus (R. Levy et al., Alterations of GABAergic neurons in the basal ganglia of patients with progressive supranuclear palsy: an in situ hybridization study of $GAD_{67}$ messenger RNA, Neurology 45:127–134, 1995). The same study affirms the potential value in patients with Steele-Richardson-Olszewski syndrome of GABAergic agonist drugs that act specifically in the GABAergic systems of the basal ganglia. The effect that we observed in Steele-Richardson-Olszewski syndrome can probably be explained on the basis of the fact that zolpidem acts in the internal segment of globus pallidus and substantia nigra pars reticulata, i.e. the GABAergic output structures of the circuits that involve the basal ganglia. In other words, zolpidem may be even more effective than L-dopa in parkinsonism plus because it is able to act on structures that, where these circuits are concerned, are "down-stream" of the striatum.

In the light of these preliminary clinical findings and the above pathophysiological considerations, it is possible that zolpidem may also have some degree of efficacy not only in PD and secondary parkinsonian syndromes but also in other extrapyramidal syndromes such as those classified under the heading of "parkinsonism plus", of which Steele-Richardson-Olszewski syndrome is one. The term "parkinsonism plus" is applied to disorders that may have a variety of symptoms other than extrapyramidal and parkinsonian signs and may be secondary to lesions of various structures (basal ganglia, substantia nigra and other encephalic structures). Syndromes classified under the heading of "parkinsonism plus" include Steele-Richardson-Olszewski syndrome, cortical-basal ganglionic degeneration, multisystem atrophy, Wilson's disease, Hallervorden-Spatz disease, Huntington's disease and neuro-acanthocytosis.

It has been demontrated that in Huntington's disease (HD) there is a selective loss of GABAergic neurons, such as striatal inhibitory projection neurons to the internal and external segment of the globus pallidus and substantia nigra pars reticulata. The selective neurodegeneration of such subpopulations of GABAergic neurons is considered a plausible explanation for the chorea and oculomotor abnormalities that are early feature of HD (R. L. Albin, Selective neurodegeneration in Huntington's Disease, Ann. Neurol. 38:835–836, 1995). The strategy of facilitating GABAergic transmission in patients with HD has been previously suggested (R. D. Adams, M. Victor, Principles of Neurology, McGraw-Hill, 1985). So far, however, the treatment of HD with GABA-mimetics drugs has met with only limited success.

According to the above-mentioned pathophysiological considerations and to our preliminary data on parkinsonism plus, imidazopyridines (including zolpidem) may be successful in the treatment of motor and cognitive symptoms of HD. Among the imidazopyridines, selective co, agonist drugs as zolpidem may in fact be considered as GABAergic agonists specific to X the GABAergic systems in the basal ganglia. Therefore, in the light of the loss of specific GABAergic neurons, imidazopyridines may represent in HD a substitutive therapy that could restore the effect of inhibition of the globus pallidus and the substantia nigra pars reticulata.

Accordingly, zolpidem is of value in the following:

(1) patients with PD and parkinsonism due to various causes (infectious agents, toxic agents, drugs, head injuries, vascular and tumoral lesions, etc.). Both in PD and parkinsonism, zolpidem can be used (either alone or in combination with L-dopa or dopamine-agonist) in patients who have ceased to respond to L-dopa or dopamine-agonists (e.g. in the advanced stages of the disease) and also in subjects in whom treatment with these drugs has been discontinued because of side effects;

(2) patients with other extrapyramidal syndromes such as those classified as "parkinsonism plus", i.e. Steele-Richardson-Olszewski syndrome (progressive supranuclear palsy), cortical-basal ganglionic degeneration, multisystem atrophy (striatonigral degeneration, Shy-Drager syndrome, olivopontocerebellar degeneration), Wilson's disease, Hallervorden-Spatz disease, Huntington's disease, neuroacanthocytosis.

As mentioned above, as well as Parkinson's disease proper, which is of idiopathic origin, there are various parkinsonian syndromes or forms of parkinsonism that may be secondary to various causes (infectious agents, toxic agents, drugs, head injuries, vascular and tumoral lesions, etc.).

Recently, a form of parkinsonism has been observed in drug addicts who had injected themselves with meperidine analogues, whose illegal synthesis had produced MPTP and MPPP.

In fact, 1-methyl-4-phenyl-1,2,3,6-tetrahydro pyridine (MPTP or N-MPTP) and 1-methyl-4-phenyl-4-propoxypiperidine (MPPP) selectively destroy the dopaminergic neurons in the substantia nigra and induce, both in man and in other primates, a parkinsonian syndrome that is similar to idiopathic Parkinson's disease in terms of its clinical, anatomopathological and biochemical appearances and drug responses (Davies et al., Chronic Parkinsonism secondary to intravenous injection of meperidine analogues, Psychiatry Res. 1, 249–254 (1979); Langston et al., Chronic Parkinsonism in humans due to a product of meperidine-analog synthesis, Science 219, 979–980 (1983); Burns et al., A primate model of parkinsonism: Selective destruction of dopaminergic neurons in the pars compacta of the substantia nigra by N-methyl-4-phenyl-1,2,3,6,-tetrahydropyridine, Proc. Natl. Acad. Sci. USA, 80, 4546–4550, July 1983).

The similarity between idiopathic Parkinson's disease and MPTP-induced parkinsonism (Burns et al.,The neurotoxicity of 1-methyl-4-phenyl-1,2,3,6,tetrahydropyridine in the monkey and man, Can. J. Neur. Sci. 11, n.1 (supplement), 166–168, February 1984) has given rise to the hypothesis that Parkinson's disease is caused by a toxin.

Although for the purposes of the present invention it is not necessary to provide or espouse any theoretical explanation of the efficacy of zolpidem in the treatment of Parkinson's disease, the following hypothesis can be put forward.

Zolpidem, unlike the benzodiazepines, causes selective inhibition both (a) of the internal segment of globus pallidus and (b) of substantia nigra pars reticulata.

(a) The inhibition of the internal segment of globus pallidus induced by zolpidem reduces the excessive inhibition by internal globus pallidus of both the thalamus and the pedunculopontine nucleus; this results in excitation of the supplementary motor area and of the descending reticulospinal and vestibulospinal pathways.

(b) The inhibition of substantia nigra pars reticulata induced by zolpidem reduces the inhibition by the substantia nigra pars reticulata of the thalamus (ventrolateral nucleus), resulting in excitation of the supplementary motor area.

We have also found that zolpidem is effective in the treatment of obsessive-compulsive disorder, other obsessive-compulsive syndromes and frontal and subcortical dementias.

Obsessive-compulsive disorder (OCD) is a psychiatric illness characterized by the recurrent appearance of obsessions (repetitive thoughts or ideas) and compulsions (repetitive behaviour, generally in response to an obsession).

The lifetime prevalence of OCD found in surveys based on interviews with subjects over the age of 18 years in the general population varies between 1.9 and 3% (L. L. Judd, L. Y. Huey, in: Harrison's Principles of Internal Medicine, McGraw-Hill, 1987).

In the pathophysiology of obsessive-compulsive disorder, a particularly important role is played by dysfunction of the circuits involving the basal ganglia (caudate nucleus, putamen and globus pallidus), the thalamus and the frontal cerebral cortex (Hymas et al., The neurology of obsessional slowness, Brain, 114:2203–2233, 1991; J. L. Cummings, K. Cunningham, Obsessive-compulsive disorder in Huntington's Disease, Biol. Psychiatry, 31:263–270, 1992; D. Laplane et al., Obsessive-compulsive and other behavioural changes with bilateral basal ganglia lesions, Brain, 112:699–725, 1989).

In patients with OCD it is often possible to detect changes in the cerebral metabolism and flow, particularly in the frontal lobe and the basal ganglia, by means of Single Photon Emission Computerized Tomography (SPECT) and Positron Emission Tomography (PET) (L. R. Baxter et al., Local cerebral glucose metabolic rates in obsessive-compulsive disorder: a comparison with rates in unipolar depression and in normal controls, Arch. Gen. Psychiatry, 44:211–218, 1987).

Numerous studies have shown that OCD or similar obsessive-compulsive syndromes can also appear in patients with neurological syndromes mostly affecting the basal ganglia (Laplane et al., Obsessive-compulsive and other behavioural changes with bilateral basal ganglia lesions, Brain, 112:699–725, 1989; Hymas et al., The neurology of obsessional slowness, Brain, 114:2203–2233, 1991). Such neurological syndromes include Gilles de la Tourette syndrome, toxic and anoxic encephalopathies, idiopathic Parkinson's disease, post-encephalitic parkinsonism, Sydenham's chorea, Huntington's disease.

Serotonin reuptake inhibitors (chlorimipramine, fluoxetine) are currently considered to be the most effective drugs for the treatment of obsessive-compulsive disorder (J. Anath, Clomipramine: an anti-obsessive drug, Can. J. Psychiatry, 31:253–258, 1986; R. Fontaine, G. Chouinard, An open clinical trial of fluoxetine in the treatment of obsessive-compulsive disorder, J. Clin. Psychopharmacol., 6:98–101, 1986). The findings regarding the efficacy of these drugs are the main indirect evidence that the serotoninergic systems are involved in the pathogenesis of obsessive-compulsive disorder (Insel et al., Obsessive-compulsive disorder and serotonin: is there a connection?, Biol. Psychiatry, 20:1174–1188, 1985).

In general, benzodiazepines have little effect on the cardinal symptoms of OCD (P. T. Lelliot, W. O. Monteiro, Drug treatment of obsessive-compulsive disorder, Drugs, 31:75–80, 1986; T. Perse, Obsessive-compulsive disorder: a treatment review, J. Clin. Psychiatry, 49:48–55, 1988). It was found that clonazepam had some beneficial effect in patients with OCD in a study conducted in a few individual patients (W. A. Hewlett et al., Clonazepam treatment of obsessions and compulsions, J. Clin. Psychiatry, 51:158–161, 1990). The drug was administered in repeated doses for a period of several months. The benefit was observed one to two weeks after the start of treatment. The authors stressed the fact that this benzodiazepine is unusual in that it influences the serotoninergic systems, albeit by mechanisms that are not fully understood (Wagner et al:, Clonazepam-induced up-regulation of serotonin- 1 and serotonin-2 binding sites in rat frontal cortex, Adv. Neurol. 43:645–651, 1986).

We examined nine patients who had been diagnosed as suffering from OCD according to the criteria of the "Diagnostic and statistical manual of mental disorders, third edition revised" (DSM III-R) (Americam Psychiatric Association, Washington D.C. 1987) to whom zolpidem had been orally administered in a single dose of 10 mg.

The demographic and clinical characteristics of the group of patients with OCD are shown in Table 5.

TABLE 5

| Characteristics of the OCD group | |
|---|---|
| Total number | n = 9 |
| Sex ratio (m/f) | 4/5 |
| Mean age (SD) | 49.6 (22.1) yrs |
| Mean disease duration (SD) | 9.2 (9.6) yrs |

A placebo-controlled double-blind study was conducted in eight patients; the drug was administered under open conditions in one patient (No. 9).

The severity of the disorder was evaluated with the Yale-Brown scale (range 0–40) (Goodmann et al., The Yale-Brown obsessive-compulsive scale, Arch.

Gen. Psychiatry, 46:1006–1011, 1989). A 25% improvement in the score was considered significant (Liebowitz et al., J. Clin. Psychopharmacol., 9:423, 1989). In four patients (Nos. 1, 2, 3, 4) the OCD was not associated with neurological disorders, the subjects concerned exhibiting only psychiatric manifestations. In the other five patients, however, the OCD was associated with neurological disorders: patient No. 5 also exhibited PD, patient No. 8 moderate dementia and patients Nos. 6, 7 and 9 a parkinsonian syndrome and dementia (mild in patient No. 6, severe in the other two).

In all four patients with dementia, the mental deterioration could be classed as subcortical dementia, with characteristics similar to those of frontal dementias (M. A. Albert et al., The subcortical dementia of progressive supranuclear palsy, J. Neurol. Neurosur. Psychiatr., 37:121–130, 1974; A. J. Lees, E. Smith, Cognitive deficits in the early stages of Parkinson's Disease, Brain, 106:257–270, 1983). In the three patients with more severe intellectual deterioration (Nos. 7, 8 and 9) it was possible only to make an evaluation using the part of the Yale-Brown scale relating to compulsions (range 0–20). The effect was assessed one hour after the administration of the drug. Table 6 shows the scores obtained on the Yale-Brown scale by the 8 patients studied under double-blind conditions, before and after the administration of placebo or zolpidem.

TABLE 6

Scores obtained on the Yale-Brown scale by the group of patients (No. 8) with OCD who took part in the double-blind study

| Y—BOCS scores: | Mean (SD) | |
|---|---|---|
| placebo | | |
| baseline | 20.7 (6.9) | |
| 1 hr after administr. | 19.5 (6.4) | p = n.s. |
| % improvement | 4.9 (15.2) | |
| zolpidem | | |
| baseline | 22.0 (7.6) | |
| 1 hr after administr. | 9.5 (6.8) | p < 0.006 |
| % improvement | 60.3 (16.9) | |

Statistical method: Wilcoxon Signed Rank Test

The results of this clinical study show that zolpidem produced a significant improvement in the symptoms in all 8 patients with OCD. The percentage of improvement in the individual patients ranged from 33% to 90%. Only patient No. 2 showed a significant response (32% improvement) to placebo; however, even in this patient the improvement produced by zolpidem was much greater than that produced by placebo. Patient No. 9, who exhibited severe dementia and received zolpidem under open conditions, showed a 33% improvement.

In three of the four patients with OCD who exhibited clinical signs of subcortical dementia of the frontal type (patients Nos. 6, 7 and 8), zolpidem administered in a single oral dose of 10 mg produced a clear improvement in the clinical signs of dementia.

A placebo-controlled double-blind neuropsychological study was conducted in patient No. 7 who had severe intellectual deterioration. After the administration of zolpidem she showed significant improvement in the tests of verbal memory, constructional praxia and deductive intelligence as well as the tests sensitive to frontal damage. Her score on Mini-Mental State Examination (M. F. Folstein et al., Mini-Mental State: a practical method for grading the mental state of patients for clinician, J. Psychiat. Res. 12:189–198, 1975) increased from 10 (poor performance) in baseline (drug-free) condition to 22 after zolpidem administration (10 mg orally), that means a performance within normal limits for her age and educational level. By contrast, her score was 8 after placebo administration. Hence patient No. 7 unexpectedly exhibited almost complete remission of the signs of dementia.

Patient No. 6, who exhibited mild intellectual deterioration and in whom zolpidem was compared with placebo under double-blind conditions, showed clinical improvement in cognitive functions and in particular in attentive functions, with remission of the dementia. Her score on Mini-Mental State Examination (MMSE) increased from 17 (baseline drug-free condition) to 24 (after zolpidem 10 mg orally), that means a performance within normal limits for her age and educational level. By contrast, her score was 18 after placebo administration.

Patient No. 8, who exhibited moderate intellectual deterioration, showed clinical improvement in cognitive functions and in particular in attentive functions, with partial remission of the dementia.

Seven of the 9 patients with OCD exhibited no signs of drowsiness. The remaining 2 exhibited mild drowsiness. A number of patients with OCD (Nos. 4, 5, 6, 7, 9) were given zolpidem orally on a long-term basis (in doses of between 20 and 60 mg/day) and in all cases the drug produced pronounced and lasting improvement in the obsessive and compulsive symptoms (decrease of Y-BOCS scores ranging from 30% to 80%).

In patients with OCD the effects of zolpidem are probably due to the inhibition of the internal segment of globus pallidus in the cortical-striatal-pallidal-thalamic circuit, as postulated above (T. R. Insel, Toward a neuro-anatomy of obsessive-compulsive disorder, Arch. Gen. Psychiatry, 49:739–744, 1992).

These results are of interest from two points of view: (a) in patients with OCD zolpidem is effective in improving the obsessive and compulsive symptoms, even after a single dose (unlike serotoninergic antidepressant, which must be administered repeatedly for several weeks before they take effect; (b) the therapeutic effect observed suggests that GABAergic systems within the cortical-striatal-pallidal-thalamic circuit may play a role in the pathophysiology of OCD.

It is interesting to note that the therapeutic response to zolpidem in patients with OCD and subcortical dementia (with characteristics identical to those of frontal dementia) is accompanied by an improvement in cognitive function. In some patients with subcortical dementia (Nos. 6 and 7) zolpidem was administered orally on a long-term basis (in doses from 30 to 60 mg/day) and produced a pronounced and lasting improvement in the cognitive deficits (increase of MMSE scores ranging from 40% to 90%).

I claim:

1. A method of treating Parkinson's disease, parkinsonian syndromes, extrapyramidal syndromes, obsessive-compulsive disorder and syndromes, and frontal and subcortical dementias, comprising administering to an animal in need of such treatment a treatment effective amount of imidazo[1,2-a]pyridine-3acetamide derivatives of the formula (I)

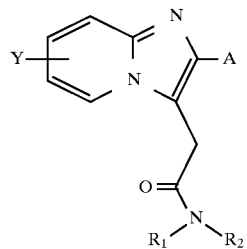
(I)

wherein
Y represents a hydrogen or halogen atom or a $C_{1-4}$ alkyl group;
A represents a naphthyl radical or a radical

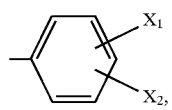

wherein each of X1 and $X_2$ independently of one another is a hydrogen or halogen atom, a $C_{1-4}$ alkoxy group, a $C_{1-6}$ alkyl group or $CF_3$, $CH_3S$—, $CH_3SO_2$— or —$NO_2$; and
each of $R_1$ and $R_2$ independently of one another represents either a hydrogen atom, or a straight or branched $C_{1-5}$ alkyl group which is unsubstituted or substituted by one or more halogen atoms, hydroxyl, —N($C_{1-4}$ alkyl)$_2$, carbamoyl or $C_{1-4}$ alkoxy groups, or an allyl group, or a propargyl group, or $C_{3-6}$ cycloalkyl group, or a benzyl group, or a phenyl group, not both R, and $R_2$ being hydrogen;
provided that, if Y is 6-chloro, A is not 4-chlorophenyl.

2. The method of claim 1, wherein the imidazo[1,2-a] pyridine-3-acetamide has the following formula (II)

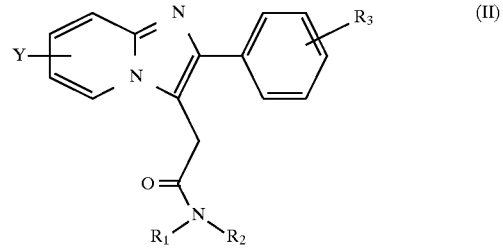

wherein
$R_3$ is halogen or a $C_{1-4}$ alkyl group;
Y is halogen or a $C_{1-4}$ alkyl group; and
each of $R_1$ and $R_2$ independently of one another represents hydrogen or a $C_{1-4}$ alkyl group, not both $R_1$ and $R_2$ being hydrogen;
provided that, if Y is 6-chloro, $R_3$ is not 4-chloro.

3. The method of claim 2, wherein the imidazo[1,2-a] pyridine-3-acetamide is zolpidem, chemical name: N,N,6-trimethyl-2-(4-methylphenyl)imidazo[1,2a]pyridine-3-acetamide hemitartrate.

* * * * *